United States Patent
McQuaid

(10) Patent No.: US 7,025,733 B2
(45) Date of Patent: Apr. 11, 2006

(54) BIOLOGICAL FLUID COLLECTION ACCESSORY DEVICE

(76) Inventor: Matthew McQuaid, 2031 Ashe St., Lakeport, CA (US) 95453

( * ) Notice: Subject to any disclaimer, the term of this patent is extended or adjusted under 35 U.S.C. 154(b) by 119 days.

(21) Appl. No.: 10/602,036

(22) Filed: Jun. 23, 2003

(65) Prior Publication Data

US 2004/0260202 A1 Dec. 23, 2004

(51) Int. Cl.
*A61B 5/00* (2006.01)
*A47K 11/00* (2006.01)
*A61M 1/00* (2006.01)
*A61F 5/44* (2006.01)

(52) U.S. Cl. ............... 600/573; 604/317; 604/347; 4/144.1; 220/731; 222/568

(58) Field of Classification Search ............. 600/573, 600/574; 604/317, 318, 346, 347, 349; 220/703, 220/704, 716–718, 731, 109, 111, 568–570; 4/144.1, 144.4

See application file for complete search history.

(56) References Cited

U.S. PATENT DOCUMENTS

| | | | |
|---|---|---|---|
| 241,863 A * | 5/1881 | Hopkins | ............. 604/347 |
| 1,657,975 A | 1/1928 | Shiells | |
| 1,928,170 A | 9/1933 | Dwork | |
| 2,309,385 A * | 1/1943 | Fleming | ............. 220/717 |
| 2,591,208 A | 4/1952 | Seymour et al. | |
| 2,628,054 A | 2/1953 | Fazakerley | |
| 2,763,402 A * | 9/1956 | Livingstone | ............. 222/109 |
| 3,161,891 A | 12/1964 | Bauman | |
| 3,172,130 A | 3/1965 | Lange | |
| 3,177,500 A | 4/1965 | Bauman | |
| 3,335,714 A | 8/1967 | Giesy | |
| D208,609 S | 9/1967 | Garland | |
| 3,473,172 A | 10/1969 | Friedman et al. | |
| 3,512,185 A | 5/1970 | Ellis | |
| 3,575,225 A | 4/1971 | Muheim | |
| 3,625,654 A | 12/1971 | Van Duyne | |
| 3,711,871 A | 1/1973 | Sherin | |
| 3,727,244 A | 4/1973 | Collins | |
| D227,413 S | 6/1973 | Sherin | |
| 3,878,571 A | 4/1975 | Seeley | |
| 3,927,426 A | 12/1975 | Geddes | |
| 4,050,103 A * | 9/1977 | Nakao et al. | ............. 4/144.3 |
| D249,997 S | 10/1978 | Lindquist | |
| 4,176,412 A | 12/1979 | Peterson | |
| D258,311 S | 2/1981 | Peterson | |
| 4,270,539 A | 6/1981 | Michaud | |
| D267,118 S | 11/1982 | Burnett | |
| D269,378 S | 6/1983 | Work | |
| 4,409,989 A | 10/1983 | Larribas | |
| 4,496,355 A | 1/1985 | Hall et al. | |
| 4,559,649 A | 12/1985 | Burnett | |
| 4,568,339 A | 2/1986 | Steer | |
| 4,681,572 A * | 7/1987 | Tokarz et al. | ............. 604/329 |
| 4,832,046 A | 5/1989 | Parrish | |

(Continued)

OTHER PUBLICATIONS

US 5,129,692, 07/1992, McCarthy (withdrawn)

*Primary Examiner*—Charles Marmor
(74) *Attorney, Agent, or Firm*—Squire, Sanders & Dempsey L.L.P.; Aaron Wininger

(57) ABSTRACT

A biological fluid collection accessory device is releasably coupled to a specimen container. The device includes an attachment ring and a peripheral wall extending from a base of the ring. The wall includes a receiving area for receiving a penis and a capturing area for capturing ejaculate.

1 Claim, 8 Drawing Sheets

U.S. PATENT DOCUMENTS

| | | | |
|---|---|---|---|
| 4,844,302 A * | 7/1989 | Lay | 222/568 |
| 4,904,248 A | 2/1990 | Vaillancourt | |
| 4,911,698 A | 3/1990 | Wapner | |
| 4,936,638 A | 6/1990 | Cross et al. | |
| 5,069,878 A * | 12/1991 | Ehrenkranz | 422/61 |
| D326,519 S | 5/1992 | Drysdale | |
| 5,129,892 A | 7/1992 | McCarthy | |
| 5,147,342 A | 9/1992 | Kane et al. | |
| D341,421 S | 11/1993 | Jones | |
| 5,295,983 A | 3/1994 | Kubo | |
| 5,422,076 A | 6/1995 | Jones | |
| D371,601 S | 7/1996 | Markles | |
| D406,644 S | 3/1999 | Keppler | |
| 5,894,608 A | 4/1999 | Birbara | |
| D409,747 S | 5/1999 | Aiken | |
| 5,920,916 A | 7/1999 | Norton | |
| D441,075 S | 4/2001 | Nara | |
| 6,299,606 B1 | 10/2001 | Young | |
| 6,398,076 B1 * | 6/2002 | Giblin et al. | 222/109 |
| 6,493,884 B1 | 12/2002 | Muller et al. | |
| 6,651,259 B1 | 11/2003 | Hartman et al. | |
| D497,425 S * | 10/2004 | McQuaid | D24/122 |
| 2003/0146226 A1 * | 8/2003 | Couto | 220/717 |

* cited by examiner

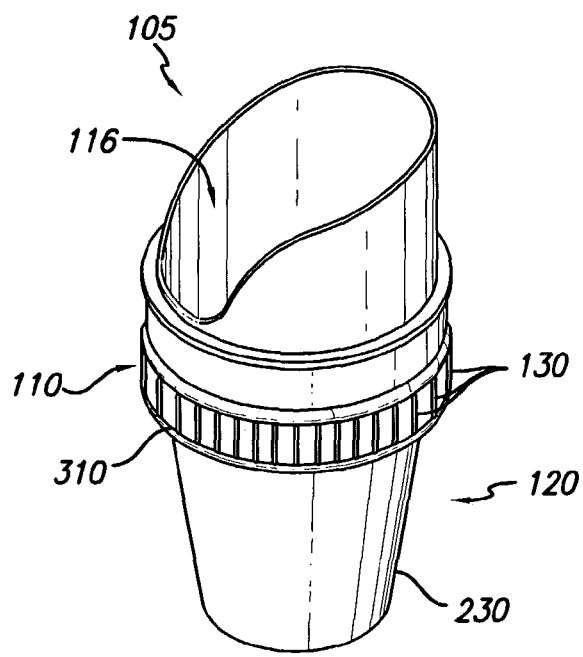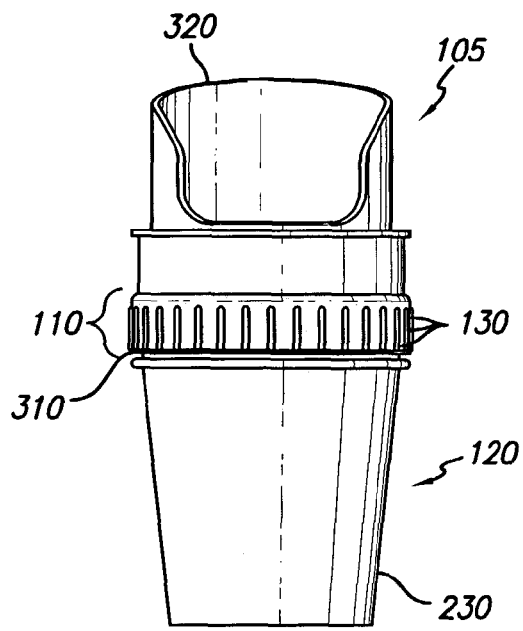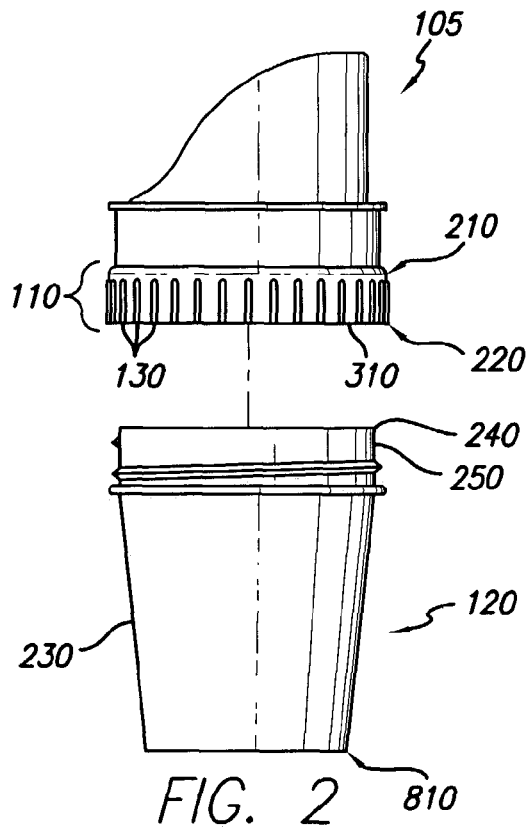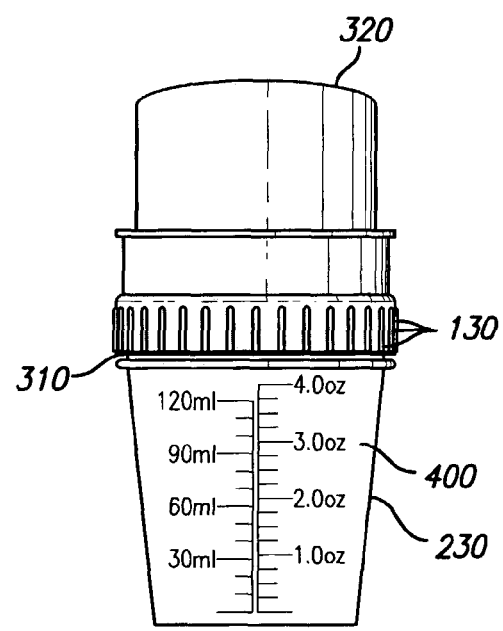
FIG. 1
FIG. 3
FIG. 2
FIG. 4

BIOLOGICAL FLUID COLLECTION ACCESSORY DEVICE

TECHNICAL FIELD

This invention relates generally to fluid collection devices, and more particularly, but not exclusively, provides a biological fluid collection device.

BACKGROUND

Semen specimen collection can be awkward and cumbersome. The shape of conventional collection containers used for semen collection can lead to inadvertent loss of early ejaculate, which can be the most sperm rich, and therefore important to capture for assisted reproduction purposes.

Another disadvantage to conventional collection containers is the discomfort they may cause during use. The superior edge of a conventional container is generally made of thin plastic, which can be uncomfortable when in contact with the genitalia.

An additional disadvantage of conventional semen collection containers and related collection procedures is the need to bend the penis from a fully erect position in order to deposit ejaculate into a conventional container. This can be difficult for many people during the ejaculation process and also lead to the loss of ejaculate. It is particularly difficult to collect ejaculate during the initial phase of ejaculation because conventional collection containers require proper angulation and alignment of the container and the penis simultaneously.

Urine collection can also be difficult using conventional collection containers, particularly for large and/or obese women, due to the shape of the containers. For example, some women may be unable to or may have difficulty positioning a conventional collection container in the urine stream in order to collect urine for tests. Pregnant women can face similar difficulties using conventional collection containers.

Accordingly, a new biological fluid collection accessory device is needed that overcomes the above-mentioned deficiencies.

SUMMARY

A specimen container attachment comprises an attachment ring and peripheral wall. The attachment ring is adapted for attachment to a specimen container. A peripheral wall extends from the attachment ring and includes a base, an outer edge, and receiving and capturing areas. The outer edge of the peripheral wall has a generally U-shaped region extending towards the base of the peripheral wall and located in the receiving area of the peripheral wall defining a generally U-shaped receiving space of the receiving area of the peripheral wall. A portion of the capturing area of the peripheral wall faces the receiving space of the receiving area of the peripheral wall.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 1 is a perspective view of a biological fluid collection accessory device coupled to a biological fluid collection container;

FIG. 2 is a right side elevational view thereof in a detached state;

FIG. 3 is a front side elevational view thereof;

FIG. 4 is a back elevational view thereof;

DETAILED DESCRIPTION

The following description is provided to enable a person having ordinary skill in the art to make and use the invention, and is provided in the context of a particular application and its requirements. Various modifications to the embodiments will be readily apparent to those skilled in the art, and the principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Embodiments of the invention increase ease in collection of liquid biological specimens, such as sperm and urine; provides a smooth receiving space for comfort during the collection process; prevents the loss of early ejaculate; prevents urine splash for obese and/or pregnant female patients; and attaches to a standard collection container.

Figure 14:
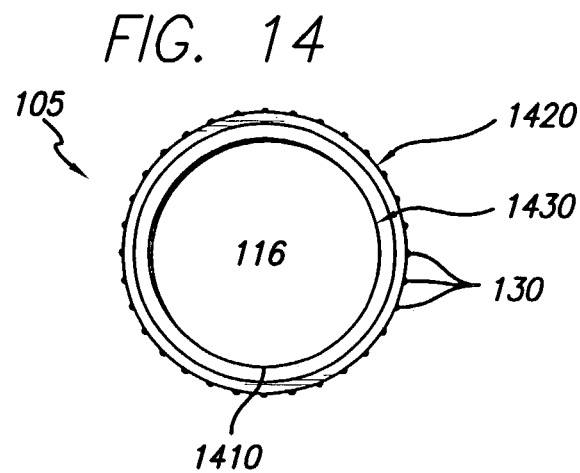
FIG. 14 is a bottom plan view thereof.
Figure 15:
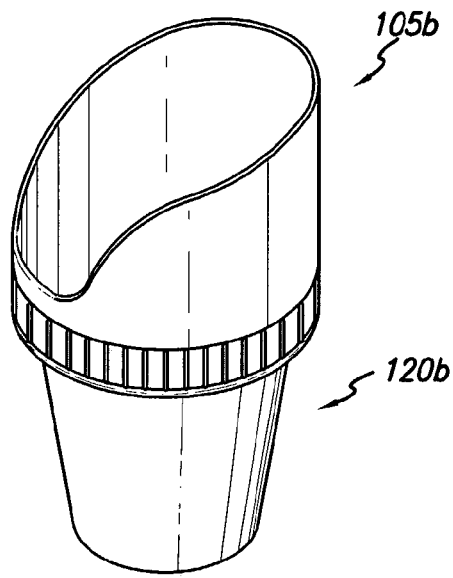
FIG. 15 is a perspective view of biological fluid collection accessory device coupled to a biological fluid collection container according to a second embodiment of the invention.
Figure 17:
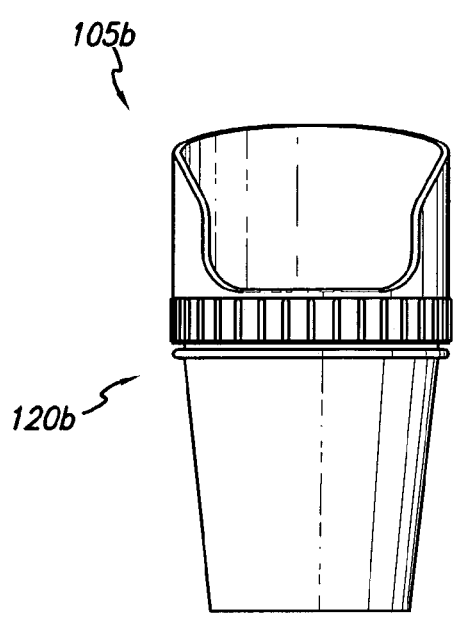
FIG. 17 is a front side elevational view thereof.
Figure 16:
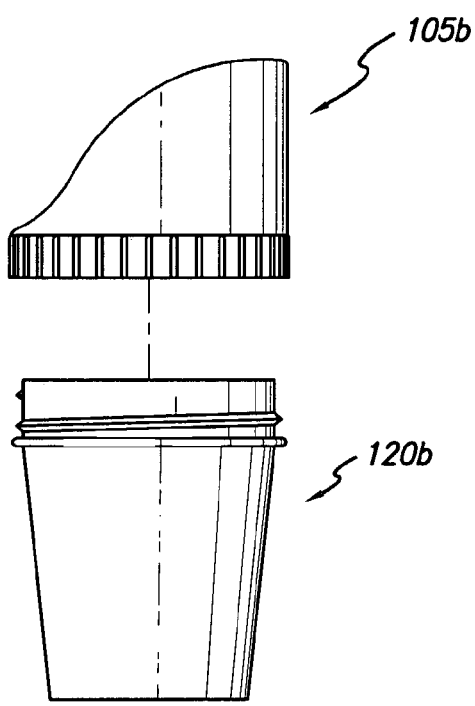
FIG. 16 is a right side elevational view thereof in a detached state.
Figure 18:
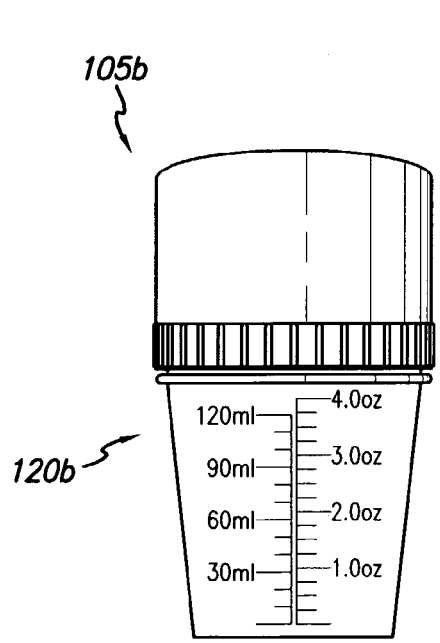
FIG. 18 is a back elevational view thereof.
Figure 19:
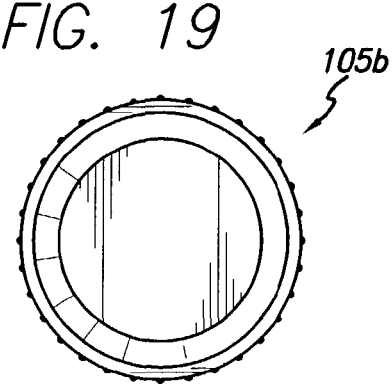
FIG. 19 is a top plan view thereof.
Figure 20:
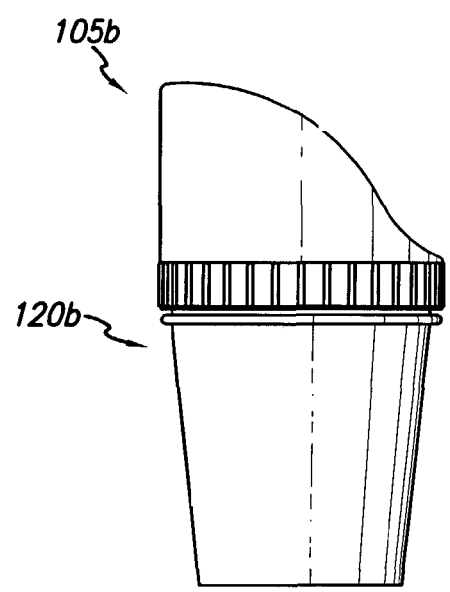
FIG. 20 is a left elevational view thereof.
Figure 21:
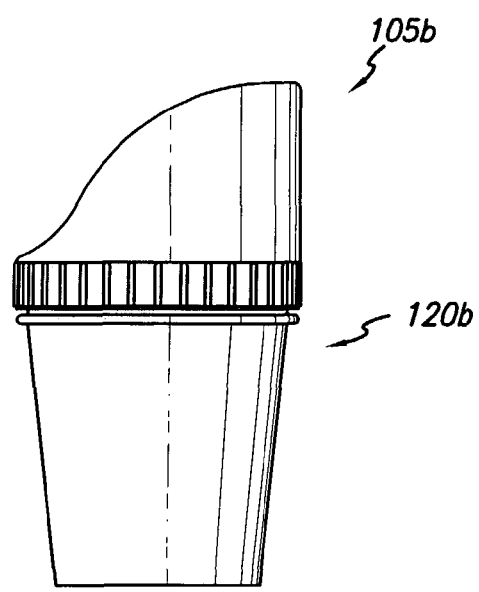
FIG. 21 is a right elevational view thereof.
Figure 22:
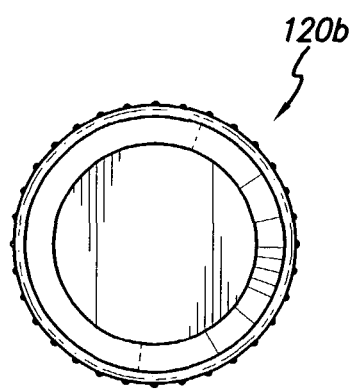
FIG. 22 is a bottom plan view thereof.
Figure 23:
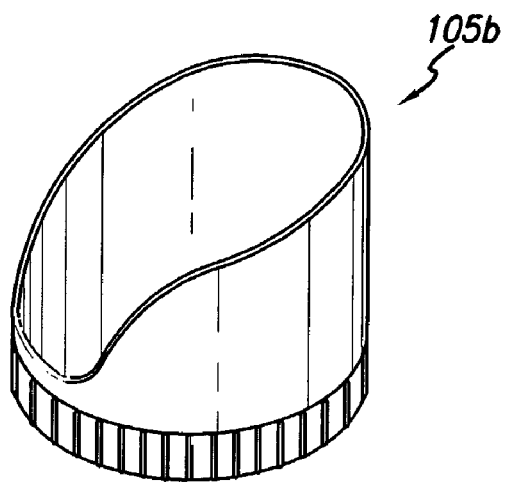
FIG. 23 is a perspective view of the biological fluid collection accessory device.
Figure 24:
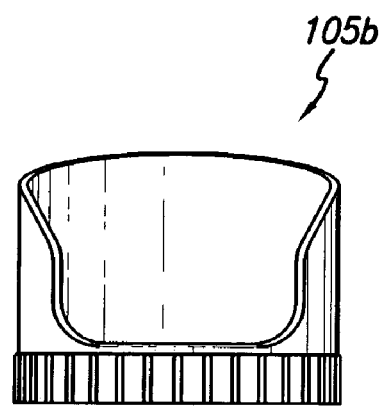
FIG. 24 is a front side elevational view thereof.
Figure 25:
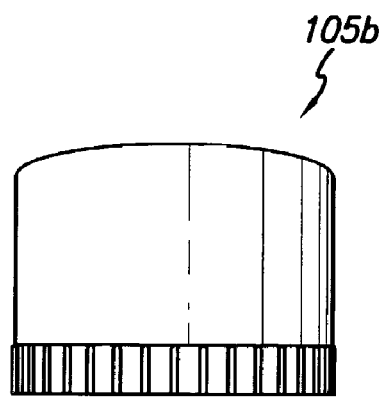
FIG. 25 is a back elevational view thereof.
Figure 26:
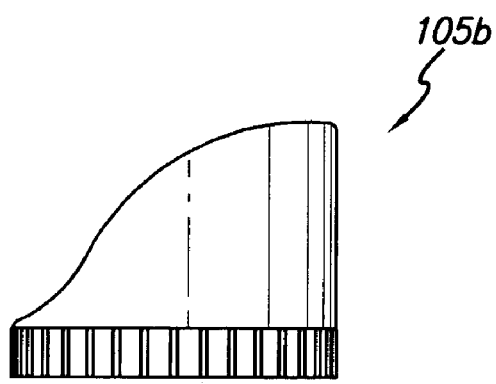
FIG. 26 is a right elevational view thereof.
Figure 27:
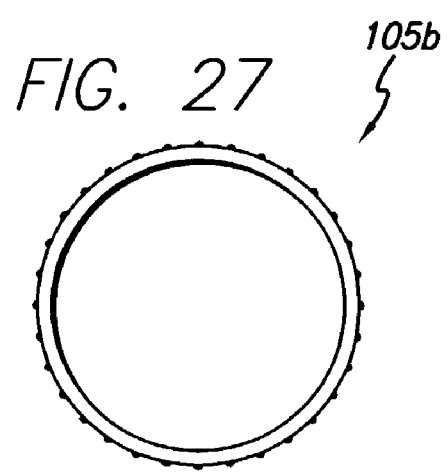
FIG. 27 is a top plan view thereof.
Figure 28:
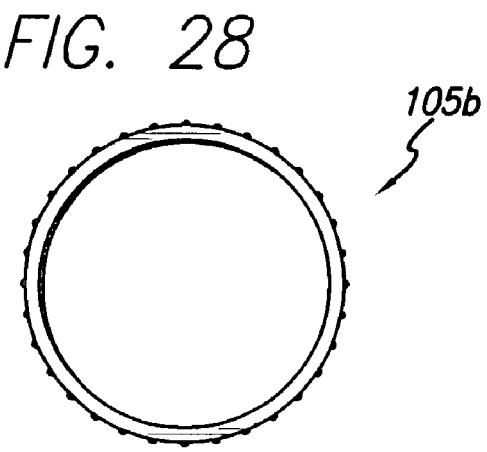
FIG. 28 is a bottom plan view thereof.

The figures show various views of a biological fluid collection accessory device 105 removeably coupled to a biological fluid collection container 120. The device 105, which is preferably sterilized before use, comprises an annular attachment ring 110 adapted for attachment to a specimen container 120, the attachment ring having an annular inner side 1430 (FIG. 14) and an outer side 1420 (FIG. 14) and generally circular top and bottom edges. The inner side 1430 of the attachment ring 110 defines a generally circular open center 116 of the attachment ring 110 to permit passage of samples including fluid samples through the attachment ring 110 into the container 120.

The attachment ring 110 has a threaded portion 1410 (FIG. 14) on the inner side 1430 of the attachment ring 110 for permitting threadable coupling of the attachment ring 110 to a biological fluid collection container 120 (also referred to interchangeably as a specimen container). The threaded portion 1410 of the attachment ring 110 is located towards the bottom edge of the attachment ring 110. In an alternative embodiment of the invention, the attachment ring 110 can have a snap-on mechanism in place of the threaded portion 1410.

The outer side 1420 of the attachment ring 110 has a plurality of elongated gripping ridges 130 for aiding the gripping of a user's fingers to the outer side 1420 of the attachment ring 110 when either screwing the attachment ring 110 on or off of the specimen container 120. The gripping ridges 130 are generally evenly spaced apart around the circumference of the outer side 1420 of the attachment ring 110. Further, the gripping ridges 130 have longitudinal axes substantially parallel with one another and the longitudinal axes of the gripping ridges 130 extend substantially perpendicular to planes defined by the top and bottom edges of the attachment ring 110.

As can be seen in FIG. 2, the gripping ridges 130 have an upper end 210 and a lower end 220. The lower ends 220 of the gripping ridges 130 are positioned adjacent the bottom edge of the attachment ring 110 while the upper ends 210 of the gripping ridges 130 are positioned towards and spaced apart from the top edge of the attachment ring 110. The upper edges 210 of the gripping ridges 130 are generally lying in a plane substantially parallel to the plane of the top edge of the attachment ring 110.

As can be seen in FIG. 3, the outer side 1420 of the attachment ring 110 has an annular lip 310 extending therearound adjacent to the bottom edge of the attachment ring 110 for further aiding the gripping of a user's fingers to the outer side 1420 of the attachment ring 110 when either screwing the attachment ring 110 on or off of the specimen container 120. The lower ends 220 of the gripping ridges 130 are in contact with (i.e., abutting) the annular lip 310 of the attachment ring 110.

A generally circular peripheral wall 320 upwardly extends from the top edge of the attachment ring 110. The peripheral wall 320 has a generally circular base (or base edge) coupled to the top edge of the attachment ring 110 and a peripheral outer (or upper) edge. The peripheral wall 320 also has opposing receiving and capturing areas with sidewalls between the receiving and capturing areas. The receiving area of the peripheral wall 320 is generally lower in height than the capturing area of the peripheral wall 320. The sidewalls are sloped downwards with either convex or concave curves to form a smooth transition between the opposing receiving and capturing areas of the peripheral wall 320.

The receiving area of the peripheral wall 320 is adapted for receiving a tip portion of a user's penis into the receiving space and has an arcuate lower portion positioned towards the base of the peripheral wall 320, which is adapted for resting thereon a portion of a user's penis extended into the receiving space. The receiving area of the peripheral wall 320 is also adapted for receiving urine when the receiving area positioned anterior to a urethral urine stream of a female.

The U-shaped region of the outer edge of the peripheral wall 320 (and especially the arcuate lower portion of the U-shaped region) has a generally smooth and rounded exterior surface adapted for enhancing the comfort of the portion of a user's penis in resting on or in contact with the U-shaped region of the outer edge of the peripheral wall 320.

An upper region of the outer edge of the peripheral wall 320 that is located in the capturing area of the peripheral wall lies in a plane spaced apart and above a plane defined by the arcuate lower portion of the U-shaped region of the outer edge of the peripheral wall 320 located in the receiving area of the peripheral wall 320. A portion of the capturing area of the peripheral wall 320 faces the generally U-shaped receiving space of the receiving area of the peripheral wall 320 so that the capturing area of the peripheral wall is adapted for deflecting semen or urine from a male or female source extended into or adjacent to the receiving area of the peripheral wall 320 down into a specimen container 120 coupled to the attachment ring 110 (i.e., the receiving area of the peripheral wall 320 can be sloped inwards). The capturing area of the peripheral wall 320 also enables capture of early ejaculate, which is the most sperm rich and therefore most useful in assisted reproduction techniques.

The plane of the upper region of the outer edge and the plane of the arcuate lower portion of the U-shaped region are spaced apart between at least 0.5 inch to about 6 inches, and preferably spaced apart between 1 inch and 3 inches, and ideally about 1.5 inches to provide an adequately sized (with respect to area) capturing region to practically suit the purposes of the capturing area.

In an embodiment where the lower arcuate region is adjacent the base of the peripheral wall 320, the capturing area of the peripheral wall may have a height defined between the plane of the upper region of the outer edge of the peripheral wall 320 in the capturing region and the base of the peripheral wall 320 in the capturing region of at least about 0.5 inch to about 6 inches, and preferably has a height between about 1 inch and about 3 inches, and ideally has a height of about 1.5 inches. The plane of the upper region of the outer edge and the plane of the arcuate lower portion of the U-shaped region are spaced apart between at least 0.5 inch to about 6 inches, and preferably spaced apart between 1 inch and 3 inches.

The outer edge of the peripheral wall 320 has a pair of sloped side regions extending between the receiving and capturing areas of the peripheral wall 320, the side regions sloping downwards from the upper region of the outer edge of the peripheral wall 320 to the U-shaped region of the outer edge of the peripheral wall 320 for providing a gradual transition between the receiving and capturing areas of the peripheral wall 320. The slopes may either be concave or convex.

Figure 5:
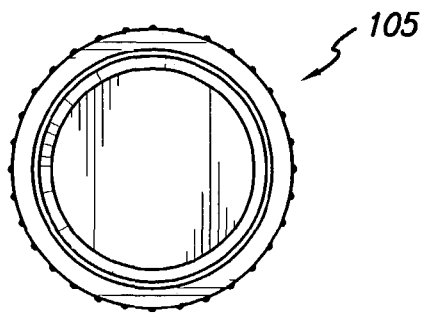
FIG. 5 is a top plan view thereof.
Figure 6:
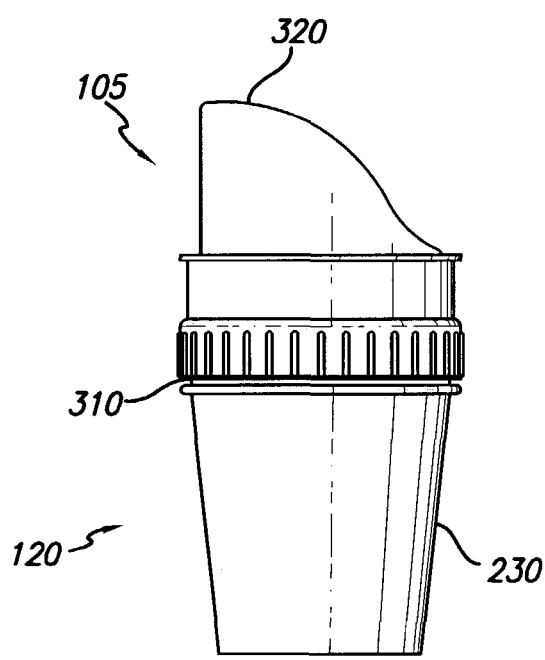
FIG. 6 is a left elevational view thereof.
Figure 7:
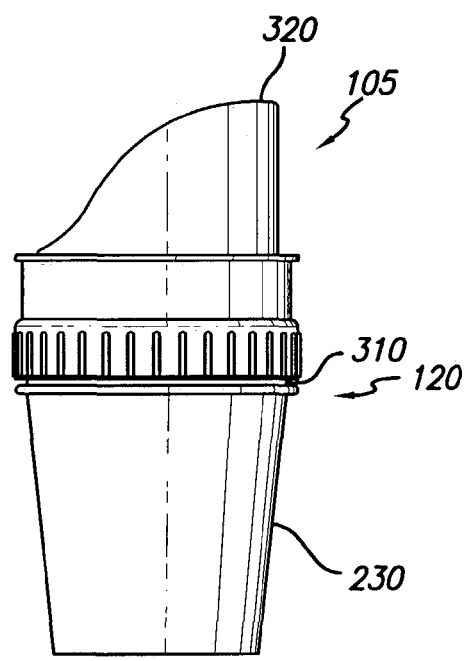
FIG. 7 is a right elevational view thereof.
Figure 8:
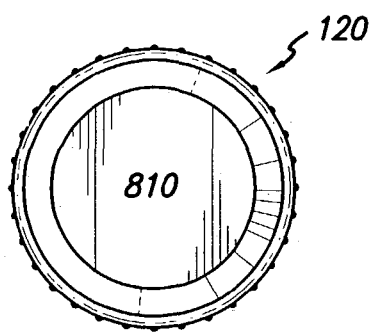
FIG. 8 is a bottom plan view thereof.
Figure 9:
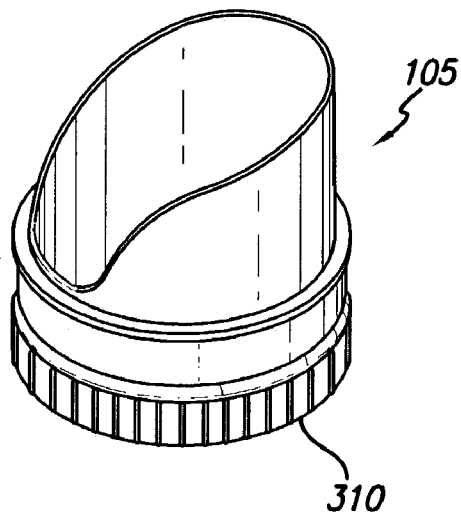
FIG. 9 is a perspective view of the biological fluid collection accessory device.
Figure 10:
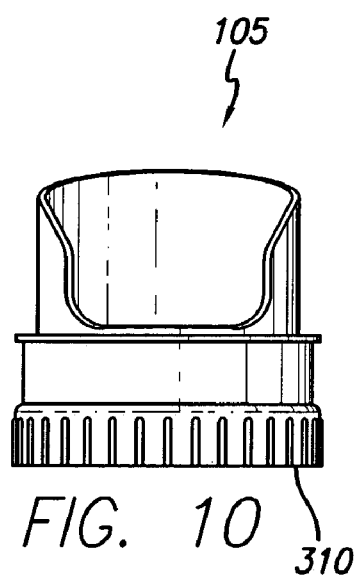
FIG. 10 is a front side elevational view thereof.
Figure 11:
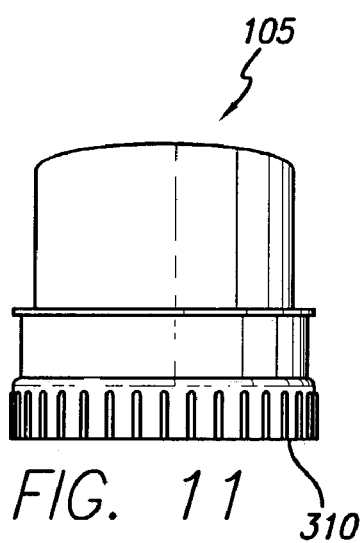
FIG. 11 is a back elevational view thereof.
Figure 12:
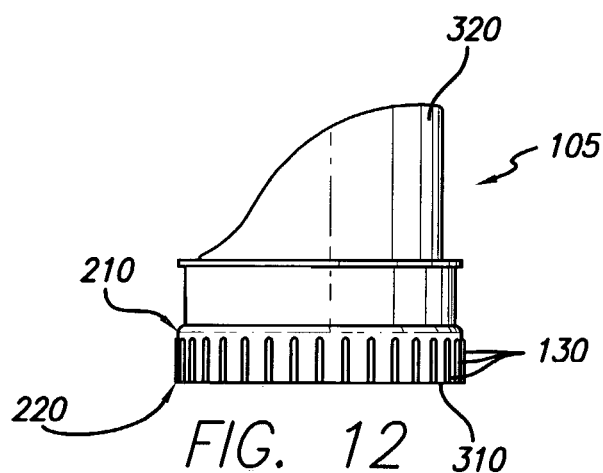
FIG. 12 is a right elevational view thereof.
Figure 13:
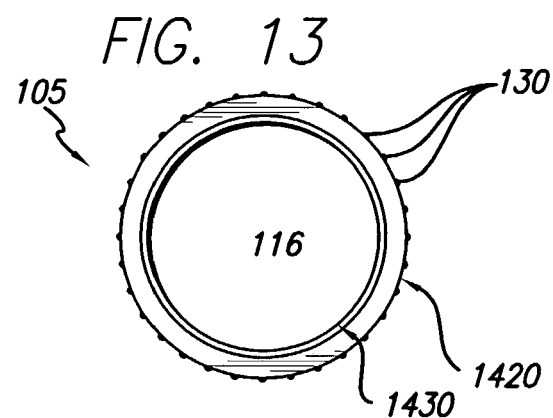
FIG. 13 is a top plan view thereof.

The specimen container 120 has a generally circular base 810 (FIG. 8) and a side wall 230 (FIG. 2) upwardly extending around a circumference of the base 810 and terminating at a generally circular upper edge 240 defining a generally circular top opening into the specimen container 120.

An outer surface of the side wall 230 of the specimen container has a threaded portion 250 adjacent the upper edge 240 of the side wall 230 of the specimen container 120 adapted for threadably mating with the threaded portions 1410 of the attachment ring 110 of the accessory device 105 to permit screwing on and off of the accessory device 105 from the specimen container 120.

The threaded portions 250 of the side wall 230 of the specimen container 120 and the attachment ring 110 of the accessory device 105 can be threadably mated together to couple the attachment ring 110 to the specimen container 120 so that the peripheral wall 320 of the accessory device 105 upwardly extends above the top opening of the specimen container 120. It will be appreciated by one of ordinary skill in the art that alternative attachments mechanisms, such as a snap on mechanism, can be used in place of or in addition to the threaded mechanism.

The specimen container 120 is adapted for receiving at least about 4.0 fluid oz (e.g., 4.5 or 5.0 oz) of a fluid substance or liquid such as semen or urine. The side wall 230 of the specimen container 120 has calibrated indicia 400 that may be used to indicate the amount of fluid held in the specimen container 120; wherein calibrated indicia include both metric (e.g., milliliters) and imperial measurements (e.g., fluid ounces).

FIG. 15 through FIG. 28 show a second embodiment of the invention that is substantially similar and operates in a substantially similar fashion to the embodiment described with respect to FIG. 1 through FIG. 14. As such, for the purpose of brevity, the FIGS. 15–28 need not be described in detail. The main difference between embodiments is that in the second embodiment, the accessory device 105*b*, which is capable of being coupled to a container 120*b*, does not include a rib between the ring 110 and the peripheral wall 320.

The foregoing description of the illustrated embodiments of the present invention is by way of example only, and other variations and modifications of the above-described embodiments and methods are possible in light of the foregoing teaching. The embodiments described herein are not intended to be exhaustive or limiting. The present invention is limited only by the following claims.

What is claimed is:

1. In combination:
   a) a specimen container attachment, comprising:
      an attachment ring adapted for attachment to a specimen container, the attachment ring having annular inner and outer sides and generally circular top and bottom edges;
      the attachment ring has a threaded portion on the inner side of the attachment ring located towards the bottom edge of the attachment ring;
      the outer side of the attachment ring having a plurality of elongated gripping ridges, the gripping ridges being generally evenly spaced apart around the outer side of the attachment ring, the gripping ridges having longitudinal axes substantially parallel with one another, the longitudinal axes of the gripping ridges extending substantially perpendicular to planes defined by the top and bottom edges of the attachment ring, the gripping ridges having upper and lower ends, the lower ends of the gripping ridges being positioned adjacent the bottom edge of the attachment ring, the upper ends of the gripping ridges being positioned towards and spaced apart from the top edge of the attachment ring, the upper ends of the gripping ridges lying in a plane substantially parallel to the plane of the top edge of the attachment ring;
      the outer side of the attachment ring having an annular lip extending therearound adjacent the bottom edge of the attachment ring, the lower ends of the gripping ridges being in contact with the annular lip of the attachment ring;
      a peripheral wall extending from the top edge of the attachment ring; the peripheral wall having a base coupled to the top edge of the attachment ring, an outer edge, and opposing receiving and capturing areas;
      the outer edge of the peripheral wall having a generally U-shaped region extending towards the base of the peripheral wall and located in the receiving area of the peripheral wall defining a generally U-shaped receiving space of the receiving area of the peripheral wall, the U-shaped region of the outer edge of the peripheral wall having an arcuate lower portion positioned towards the base of the peripheral wall, the U-shaped region of the outer edge of the peripheral wall having a generally smooth and rounded exterior surface;
      an upper region of the outer edge of the peripheral wall located in the capturing area of the peripheral wall lying in a plane spaced apart and above a plane defined by the U-shaped region of the outer edge of the peripheral wall located in the receiving area of the peripheral wall, a portion of the capturing area of the peripheral wall facing the receiving space of the receiving area of the peripheral wall; and
      the outer edge of the peripheral wall having a pair of side regions extending between the receiving and capturing areas of the peripheral wall, the side regions sloping downwards from the upper region of the outer edge of the peripheral wall to the U-shaped region of the outer edge of the peripheral wall; and
   b) a specimen container having a base and a side wall upwardly extending around the base and terminating at an upper edge that defines a top opening into the specimen container;
      the side wall of the specimen container having a threaded portion adjacent the upper edge of the side wall of the specimen container; and
      the threaded portions of the side wall of the specimen container and the attachment ring of the specimen container attachment being threadably mated together to couple the attachment ring to the specimen container so that the peripheral wall of the specimen container attachment upwardly extends above the top opening of the specimen container.

\* \* \* \* \*